United States Patent [19]

Cimiluca

[11] Patent Number: 5,641,512
[45] Date of Patent: Jun. 24, 1997

[54] SOFT GELATIN CAPSULE COMPOSITIONS

[75] Inventor: Paul Alfred Cimiluca, Cincinnatti, Ohio

[73] Assignee: The Procter & Gamble Company, Cincinnati, Ohio

[21] Appl. No.: 412,627

[22] Filed: Mar. 29, 1995

[51] Int. Cl.$^6$ .................... A61K 9/48; A61K 9/66
[52] U.S. Cl. ............... 424/455; 424/451; 424/452
[58] Field of Search ................... 424/451, 452, 424/455

[56] References Cited

U.S. PATENT DOCUMENTS

| | | | |
|---|---|---|---|
| 2,786,767 | 3/1957 | Novak | 99/140 |
| 3,389,194 | 6/1968 | Somerville | 264/4 |
| 3,632,742 | 1/1972 | Eckert et al. | 424/37 |
| 3,784,684 | 1/1974 | Bossert et al. | 424/37 |
| 3,851,051 | 11/1974 | Miskel et al. | 424/37 |
| 3,865,603 | 2/1975 | Szymanski et al. | 106/130 |
| 4,158,068 | 6/1979 | Lipinski et al. | 426/548 |
| 4,251,195 | 2/1981 | Suzuki et al. | 425/6 |
| 4,422,985 | 12/1983 | Morishita et al. | 254/4.4 |
| 4,426,337 | 1/1984 | Suzuki et al. | 264/4 |
| 4,481,157 | 11/1984 | Morishita et al. | 264/4.1 |
| 4,762,719 | 8/1988 | Forester | 424/440 |
| 4,808,410 | 2/1989 | Sorrentino et al. | 424/435 |
| 4,888,140 | 12/1989 | Schlameus et al. | 264/4.3 |
| 4,935,243 | 6/1990 | Borkan et al. | 424/441 |
| 5,071,643 | 12/1991 | Yu et al. | 514/570 |
| 5,141,961 | 8/1992 | Coapman | 514/629 |
| 5,173,304 | 12/1992 | Lohner et al. | 424/456 |
| 5,300,305 | 4/1994 | Stapler et al. | 424/490 |
| 5,360,615 | 11/1994 | Yu et al. | 424/455 |
| 5,370,864 | 12/1994 | Peterson et al. | 424/49 |
| 5,376,688 | 12/1994 | Morton et al. | 514/786 |
| 5,405,616 | 4/1995 | Wunderlich et al. | 424/451 |
| 5,407,665 | 4/1995 | McLaughlin et al. | 424/55 |
| 5,431,916 | 7/1995 | White | 424/451 |
| 5,458,879 | 10/1995 | Singh et al. | 424/400 |
| 5,484,606 | 1/1996 | Dhabhar | 424/455 |

FOREIGN PATENT DOCUMENTS

| | | | |
|---|---|---|---|
| 121321 | 10/1984 | European Pat. Off. | A61K 9/48 |
| 0631782A1 | 1/1995 | European Pat. Off. | A61K 31/52 |
| 1060258 | 1/1967 | United Kingdom . | |
| WO94/25008 | 11/1994 | WIPO | A61K 9/48 |
| 9504527 | 2/1995 | WIPO . | |
| WO95/04527 | 2/1995 | WIPO | A61K 31/165 |

OTHER PUBLICATIONS

"Soft Gelatin Capsules I: Factors Affecting Capsule Shell Dissolution Rate", F. S. Hom, S. A. Veresh, J. J. Miskel, Journal of Pharmaceutical Sciences, vol. 62, No. 6, Jun. 1973.
Fundamentals of Polymer Processing, pp. 484–493.
U.S. application No. 08/054762, White, filed Apr. 29, 1993.
U.S. application No. 08/185,576, Dhabhar, filed Jan. 24, 1994.
U.S. application No. 08/185,652, Dhabhar, filed Jan. 24, 1994.
U.S. application No. 08/204,932, Dhabhar, filed Mar. 2, 1994.
U.S. application No. 08/370,332, Rankell et al., filed Jan. 9, 1995.

*Primary Examiner*—Shep K. Rose
*Attorney, Agent, or Firm*—David K. Dabbiere; Douglas C. Mohl; Mary Catherine Poland

[57] ABSTRACT

The present invention relates to improved pharmaceutical compositions containing an analgesic encapsulated within a soft gelatin shell wherein said shell contains a xanthine derivative, such as caffeine.

10 Claims, No Drawings

SOFT GELATIN CAPSULE COMPOSITIONS

TECHNICAL FIELD

The present invention relates to improved pharmaceutical compositions containing an analgesic encapsulated within a soft gelatin shell wherein said shell contains a xanthine derivative, such as caffeine.

BACKGROUND OF THE INVENTION

Liquid, and especially concentrated liquid pharmaceutical compositions offer many advantages over solid compositions. Liquids are easy to swallow and provide an excellent vehicle for the uniform delivery of pharmaceutical actives. Liquids provide a rapid onset of pharmacologic action, since the composition does not first have to disintegrate and dissolve in the gastrointestinal tract. Concentrated liquid compositions are ideally suited for encapsulation within a soft gelatin shell, to provide a portable and easy-to-swallow soft, flexible capsule. Encapsulation would also permit the accurate and uniform delivery of a unit dose of a pharmaceutical active, an advantage which becomes especially important when relatively small amounts of an active are to be delivered. Additionally, soft gelatin capsules are aesthetically appealing (especially when filled with a transparent liquid) and can be manufactured in a wide variety of sizes, shapes, and colors.

However, despite these advantages of liquid compositions, it is not always possible to prepare a liquid composition of the desired pharmaceutical active. In many instances the components to be solubilized are not compatible with one another, or require higher solvents. Also, it may not be possible or desirable to incorporate water, water-miscible co-solvents, or surfactants into a pharmaceutical composition. For example, certain water-miscible co-solvents may be relatively volatile, thereby resulting in concentration changes in the actives over time. Also, these co-solvents may not be compatible with the desired pharmaceutical actives.

Previous investigators have attempted to circumvent these incompatibility problems by modifying the gelatin in the capsule shell. For example, U.S. Pat. No. 3,865,603, to Szymanski et at., issued Feb. 11, 1975 discloses gelatin compositions which are extended with chemically modified fluidity starches; U.S. Pat. No. 2,580,683, to Kreuger, issued Jan. 1, 1952 discloses gelatin compositions modified by the addition of non-hygroscopic water soluble substances; and Japanese Patent No. 84044096, to Morishita, issued Jan. 26, 1984 discloses gelatin shells modified with tannic acid, and sugar and/or sugar derivatives. However, it may not always be desirable, feasible or economical to modify the soft gelatin shell with such additives. The present inventor has found incorporating a specific component in the outer gelatin shell, i.e., a xanthine derivative overcomes incompatability problems with an analgesic active.

It is therefore an object of the present invention to provide a soft gelatin capsules containing an analgesic pharmaceutical actives and xanthine or xanthine derivative wherein said xanthine or xanthine derivative is incorporated into the gelatin shell.

These and other objects of this invention will become apparent in light of the following disclosure.

SUMMARY OF THE INVENTION

The present invention relates to pharmaceutical compositions in the form of a soft gelatin capsule comprising:

a) an outer gelatin shell comprising a xanthine derivative; and b) a concentrated liquid core composition comprising a safe and effective amount of at least one analgesic pharmaceutical active.

The present invention also relates to a process for preparing soft gelatin capsules containing a solution of a difficultly soluble pharmaceutical active, and to the compositions and the filled capsules themselves.

All percentages and ratios used herein are by weight and all measurements are at 25° C., unless otherwise indicated.

DETAILED DESCRIPTION OF THE INVENTION

Liquid Pharmaceutical Core Compositions

The concentrated liquid pharmaceutical compositions of the present invention comprise the following essential, as well as optional, components.

Analgesic Pharmaceutical Actives

Useful analgesic pharmaceutical actives in the compositions of the present invention include aspirin and acetaminophen as well as the non-steroidal anti-inflammatory drugs (NSAIDS) selected from the following categories: propionic acid derivatives; acetic acid derivatives; fenamic acid derivatives; biphenylcarboxylic acid derivatives; and oxicams. All of these NSAIDS are fully described in the U.S. Pat. No. 4,985,459 to Sunshine et al., issued Jan. 15, 1991, incorporated by reference herein. Particularly preferred are the dextrorotatory or S(+) isomers of these agents.

Examples of preferred analgesic pharmaceutical actives useful in the present invention include, but are not limited to, acetaminophen, acetylsalicylic acid, ibuprofen, fenbuprofen, fenoprofen, flurbiprofen, indomethacin, ketoprofen, naproxen, their pharmaceutically-acceptable salts, enantiomers thereof, and mixtures thereof. Acetaminophen, ibuprofen and naproxen are especially preferred for use in the compositions of the present invention.

The term "pharmaceutically acceptable salts" refers to salts prepared from pharmaceutically acceptable non-toxic bases including inorganic bases and organic bases. Salts derived from nonorganic bases include sodium, potassium, lithium, ammonia, calcium, magnesium, ferrous, zinc, manganous, aluminum, ferric, manganic salts and the like. Salts derived from pharmaceutically acceptable organic non-toxic bases include salts of primary, secondary, tertiary and quaternary amines, substituted amines including naturally occurring substituted amines, cyclic amines and basic ion exchange resins, such as triethylamine, tripropylamine, 2-dimethylaminoethanol, 2-diethylaminoethanol, lysine, arginine, histidine, caffeine, procaine, N-ethylpiperidine, hydrabamine, oholine, betaine, ethylenediamine, glucosamine, methylglycamine, theobromine, purines, piperazine, piperidine, polyamine resins and the like.

Additional Pharmaceutical Actives

The liquid pharmaceutical core compositions of the instant invention can also contain one or more additional pharmaceutical actives. Useful classes of additional pharmaceutically-active compounds include antipyretics, calcium channel blockers, beta-blockers, antibacterials, antidepressants, antidiabetics, anti-emetics, antihistamines, cerebral stimulants, sedatives, anti-parasitics, expectorants, diruetics, decongestants, antitussives, muscle relaxants, anti-Parkinsonian agents, bronchodilators, cardiotonics, antibiotics, antivitals, nutritional supplements (such as vitamins, minerals, fatty acids, amino acids, and the like), and mixtures thereof.

Examples of additional pharmaceutical actives useful in the present invention include, but are not limited to, pseudoephedrine and its salts such as pseudoephedrine hydrochloride; dextromethorphan and its salts such as dextromethorphan hydrobromide; doxylamine and its salts such as doxylamine succinate; phenindamine and its salts such as phenindamine hydrogen tartrate; pheniramine and its salts such as pheniramine maleate; chlorpheniramine and its salts such as chlorpheniramine maleate; ephedrine and its salts such as ephedrine sulfate; triprolidine and its salts such as triprolidine hydrochloride; diphenhydramine and it salts such as diphenhydramine hydrochloride, diphenhydramine titrate, and diphenhydramine 8-chlorotheophyllinate; phenyltoxyl- amine and its salts; guaifenesin; phenylpropanolamine hydrochloride; and mixtures thereof. Preferred additional pharmaceutical actives are dextromethorphan hydrobromide, doxylamine succinate, pseudoephedrine hydrochloride, chlorpheniramine maleate, guaifenesin, triprolidine hydrochloride, diphenydramine hydrochloride and mixtures thereof.

The concentrated liquid core compositions of the instant invention optionally comprises adding from about 0.5% to about 20% of such a second pharmaceutical active, or mixtures thereof.

Solvents

A sufficient quantity of solvent is utilized to aid in the solubilization of the analgesic active. By "sufficient" is meant a quantity of solvent that will ensure solubility of the components of the composition and yet not dilute the composition to the point where it occupies an unreasonably large volume. The solubilizing agent for the analgesic active can be any of a number of materials. After mixing and solubilization of the components of the instant invention, any solvents with sufficiently low boiling points such as an alcohol can be removed using standard evaporation techniques until the composition is substantially free from such solvents. Preferably the compositions comprise no more than from about 0.1% to about 6% of such solvents after the evaporation step.

Particularly preferred solvents include polyethylene glycols, polyvinylpyrrolidone and propylene glycol. These solvents are fully described in U.S. Pat. No. 5,141,961 to Coapman, issued Aug. 25, 1992 which is incorporated by reference herein. Also useful are other glycols such as butylene glycol and hexylene glycol.

Polyethylene glycols generally are clear, viscous liquids or white solids which are soluble in water and many organic solvents. These polymers correspond to the general formula:

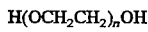

where n is greater than or equal to 4. The polyethylene glycols useful herein are those which are liquids at room temperature or have a melting point slightly thereabove. Preferred are the polyethylene glycols having a molecular weight range from about 300 to about 1000 and corresponding n values from about 6 to about 20. More preferred are the polyethylene glycols having a molecular weight range from about 400 to about 1000 and corresponding n values from about 8 to about 20. Moreover, mixtures of two or more polyethylene glycols of different average molecular weight range or n value can also be employed in the present invention. Liquid and low-melting polyethylene glycols are commercially available from Union Carbide (Danbury, Conn.) under the Carbowax® trademark. See "Carbowax® Polyethylene Glycols", Union Carbide Technical Bulletin f-4772M-ICD 11/86-20M, this reference being incorporated herein by reference in its entirety.

Polyvinylpyrrolidone has different solubility characteristics based on its polymeric structure. Long-chain polyvinylpyrrolidone, which is also known as povidone, has good solubility in water and a number of organic solvents. Crosslinked polyvinylpyrrolidone, which is also known as crospovidone, is insoluble in virtually all common solvents. Both the soluble and insoluble forms of polyvinylpyrrolidone are commercially available from GAF Chemicals Company (Wayne, N.J.) under the Plasdone® and Polyplasdone® trademarks, respectively, and from BASF Aktiengesellschaft (Ludwigshafen, Germany) under the Kollidon® trademark. Soluble forms of polyvinylpyrrolidone include Plasdone® K-25, Plasdone® K-26/28, Plasdone® K-29/32, Plasdone® C-15, Plasdone® C-30, Plasdone® C-90, Kollidon®12 PF, Kollidon®17 PF, Kollidon®25, Kollidon®30, and Kollidon® 90. Insoluble forms of polyvinylpyrrolidone include Polyplasdone XL®, Polyplasdone XL®10, Kollidon® CL, and Kollidon® CL-M. See "Tableting With Plasdone®", GAF Technical Bulletin 2302-110R1 (1986); "Polyplasdone XL®, Polyplasdone XL®10", GAF Technical Bulletin 2302-099 R2 (1984); and "Kollidon® Grades, Polyvinylpyrrolidone for the Pharmaceutical Industry", BASF Technical Bulletin MEF 129e, Register 2, May 1986 (Bn); these references being incorporated herein by reference in their entirety.

The soluble forms of polyvinylpyrrolidone are preferred for use in the present invention. Preferred are soluble polyvinylpyrrolidones having an average molecular weight in the range from about 2900 to about 1,100,000; more preferred are those having an average molecular weight in the range from about 9000 to about 45,000; and most preferred are those having an average molecular weight of about 29,000. Moreover, mixtures of two or more soluble polyvinylpyrrolidones of different average molecular weight can be employed.

Propylene Glycol

Propylene glycol, which is represented by the formula:

is well known in the art for its solvent and/or humectant properties and is described in *Hawley's Condensed Chemical Dictionary*, pp. 970–971, (Revised by Richard J. Lewis, Sr.) (12th ed. 1993), herein incorporated by reference. Propylene glycol suitable for use in the present invention is obtainable from any number of suppliers, Dow Chemical being one.

The liquid core compositions of the instant invention comprises adding from about 1% to about 50% of solvent, more preferably from about 5% to about 40%, and most preferably from about 10% to about 30%. Suitable solvents which include polyethylene glycol, propylene glycol polyvinylpyrrolidone are preferred as the solvent for use in the processes of the instant invention and are discussed briefly below.

Optional Components for Liquid Core

Other components which can be incorporated into the liquid pharmaceutical core compositions of the instant invention include colorings, flavorings, preservatives, lubricants, flow-enhancers, filling aids, anti- oxidants, essences, and other aesthetically pleasing components.

Process for Solubilizing Pharmaceutical Actives

The concentrated liquid cores containing pharmaceutical actives are prepared using art-recognized principles and methodologies in mixing the ingredients together and in choosing the type of mixing equipment to be used. In a preferred manner of execution, the analgesic pharmaceutical active, polyethylene glycol, polyvinylpyrrolidone, and solvent are combined and mixed until dissolved to form a homogeneous solution. Any optional components can either be added initially or after the essential components are combined.

Next, any volatile solvent is removed from the resulting homogeneous solution until the residual amount of solvent is present at no more than from about 0.1 percent to about 6 percent by weight of the composition. Such solvents can be removed using any art-recognized evaporation techniques including, but not limited to, rotary evaporation, spray-drying, flash evaporation, film evaporation, freeze-drying, thin film evaporation, forced circulation evaporation, wiped film evaporation, falling film evaporation, and the like. This resulting solution is suitable for encapsulation in a soft gelatin capsule using standard encapsulation techniques.

Soft Gelatin Capsules

Preselected amounts of the liquid core pharmaceutical compositions of the present invention are encapsulated in a soft gelatin shell containing a xanthine derivative described below. Optionally, the soft gelatin shell is essentially transparent so as to enhance the aesthetic qualities of the capsule. The soft gelatin shells comprise the following essential, as well as optional, components.

Gelatin

Gelatin is an essential component of the soft gelatin shells of the instant invention. The starting gelatin material used in the manufacture of soft capsules is obtained by the partial hydrolysis of collagenous material, such as the skin, white connective tissues, or bones of animals. Gelatin material can be classified as Type A gelatin, which is obtained from the acid-processing of porcine skins and exhibits an isoelectric point between pH 7 and pH 9; and Type B gelatin, which is obtained from the alkaline-processing of bone and animal (bovine) skins and exhibits an isoelectric point between pH 4.7 and pH 5.2. Blends of Type A and Type B gelatins can be used to obtain a gelatin with the requisite viscosity and bloom strength characteristics for capsule manufacture. Gelatin suitable for capsule manufacture is commercially available from the Sigma Chemical Company, St. Louis, Mo. For a general description of gelatin and gelatin-based capsules, see *Remington's Pharmaceutical Sciences*, 16th ed., Mack Publishing Company, Easton, Pa. (1980), page 1245 and pages 1576–1582; and U.S. Pat. No. 4,935,243, to Borkan et at., issued Jun. 19, 1990; these two references being incorporated herein by reference in their entirety.

The soft gelatin shell of the capsules of the instant invention, as initially prepared, comprises from about 20% to about 60% gelatin, more preferably from about 25% to about 50% gelatin, and most preferably from about 40% to about 50% gelatin. The gelatin can be of Type & Type B, or a mixture thereof with bloom numbers ranging from about 60 to about 300.

Plasticizer

A plasticizer is another component of the soft gelatin shells of the instant invention. One or more plasticizers is incorporated to produce a soft gelatin shell. The soft gelatin thus obtained has the required flexibility characteristics for use as an encapsulation agent. Useful plasticizers of the present invention include glycerin, sorbitan, sorbitol, or similar low molecular weight polyols, and mixtures thereof.

The shell of the present invention, as initially prepared, generally comprises from about 10% to about 35% plasticizer, preferably from about 10% to about 25% plasticizer, and most preferably from about 10% to about 20% plasticizer. A preferred plasticizer useful in the present invention is glycerin.

Water

The soft gelatin shells of the instant invention also comprise water. Without being limited by theory, the water is believed to aid in the rapid dissolution or rupture of the soft gelatin shell upon contact with the gastrointestinal fluids encountered in the body.

The shell of the present invention, as initially prepared, generally comprises from about 15% to about 50% water, more preferably from about 25% to about 40% water, and most preferably from about 30% to about 40% water.

Xanthine Derivatives

A xanthine derivative is incorporated into the soft gelatin shell of the present invention.

The term "xanthine derivative" as used herein are defined as xanthine or a compound comprising the xanthine nucleus substituted with the substitutents defined hereinafter as well as any pharmaceutical acceptable salts or esters thereof (e.g., acid addition salts such as acetate, benzoate, salicylate, and alkaline salts thereof) complexes, double salts and mixtures. The xanthine derivatives of the invention comprise compounds of the general formula:

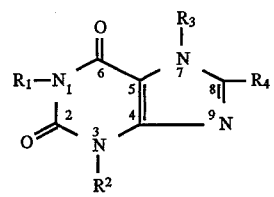

or a pharmaceutically acceptable non-toxic salt thereof wherein $R_1$–$R_3$, inclusive independently represent hydrogen $C_1$–$C_6$ alkyl (straight or branched), $C_1$–$C_6$ alkoxy, $C_1$–$C_6$ haloalkyl, $C_3$–$C_6$ cycloalkyl, hydroxy ($C_1$–$C_6$) alkyl, halogen, hydroxy ($C_1$–$C_4$) alkylamino ($C_1$–$C_4$) alkyl, $C_1$–$C_4$ (dialkyl)amino($C_1$–$C_4$)alkyl, $C_1$–$C_4$ alkylcarbonyl($C_1$–$C_4$) alkyl, $C_1$–$C_6$alkylamino, $C_1$–$C_6$(dialkyl)amino, indoloyn, phenyl or allyl.

$R_4$ is hydrogen, $C_1$–$C_6$alkyl, halo($C_1$–$C_6$) alkyl, $C_1$–$C_6$alkylamino, $C_1$–$C_6$alkylthio, nitro, carboxy, $C_1$–$C_6$ (dialkyl)amino, $C_3$–$C_6$cycloalkyl, phenyl, naphthyl, ar($C_1$–$C_4$)alkyl, or a group of the formula:

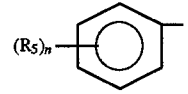

where $R_5$ is halo, $C_1$–$C_6$ alkyl, $C_1$–$C_6$alkyl, $C_1$–$C_6$alkoxy, $C_1$–$C_6$alkylthio, nitro or $C_1$–$C_6$alkylamino and n is 1, 2 or 3.

Exemplary preferred compounds within the scope of the above xanthine derivatives formula include caffeine, pentoxifylline, theophylline, theobromine, bamifylline, diprophylline, 1-methylxanthine, 1-methyl-8-methylxanthane, 8-phenyl-1-methylxanthine, 1,7-dimethylxanthine, 1,3-dimethylxanthine, 8-methyltheophylline, 8-ethyltheophylline, 8-nitrotheophylline, 8-methylaminotheophylline, 8-dimethylaminotheophylline, 8-methyltheophylline, 8-ethyltheophylline, 8-(ethylpropionate)theophylline, 8-cyclopropyltheophylline, 8-cydopentyltheophylline, 8-cyclohexyltheophylline, 8-phenyltheophylline, 8-(para-chlorophenyl)theophylline, 8-bromophenyl)theophylline, 8-(para-methoxyphenyl)theophylline, 8-(para-nitrophenyl)

theophylline, 8-(dimethylaminophenyl)theophylline, 8-(methylphenyl)theophylline, 8-(3,4-dichlorophenyl) theophylline, 8-(meta-nitrophenyl) theophylline, 8-(ortho-nitrophenyl)theophylline, 8-(1-napththyl)theophylline, 8-(2,6-dimethyl-4-hydroxyphenyl)theophylline, 7-(2-chloroethyl)theophylline, 1-methyl-3,7-diethylxanthine, 1-methyl-3-isobutylxanthine, 1-ethyl-3,7-dimethylxanthine, 1,3-diethylxanthine, 1-ethyl-3-propyl-7-butyl-8-methylxanthine, 1,3-dipropylxanthine, 1,3-diethylxanthine and 1-butyl-3,7-dimethylxanthine. Most preferred for use herein are caffeine and pentoxifylline.

Other optional components which can be incorporated into the soft gelatin shells include colorings, flavorings, preservatives, anti-oxidants, essences, and other aesthetically pleasing components.

Soft Gelatin Shell Preparation and Encapsulation

The solubilized pharmaceutical compositions of the present invention can be encapsulated within any conventional soft gelatin shell that is capable of substantially containing the composition for a reasonable period of time. The soft gelatin shells of the instant invention can be prepared by combining appropriate amounts of gelatin, water, plasticizer, xanthine derivative and any optional components in a suitable vessel and agitating and/or stirring while heating to about 65° C. until a uniform solution is obtained. This soft gelatin shell preparation can then be used for encapsulating the desired quantity of the solubilized fill composition employing standard encapsulation methodology to produce one-piece, hermetically-sealed, soft gelatin capsules. The gelatin capsules are formed into the desired shape and size so that they can be readily swallowed. The soft gelatin capsules of the instant invention are of a suitable size for easy swallowing and typically contain from about 100 mg to about 2000 mg of the solubilized pharmaceutical active composition. Soft gelatin capsules and encapsulation methods are described in P. K. Wilkinson et at., "Softgels: Manufacturing Considerations", *Drugs and the Pharmaceutical Sciences*, 41 (*Specialized Drug Delivery Systems*), P. Tyle, Ed. (Marcel Dekker, Inc., New York, 1990) pp.409–449; F. S. Horn et at., "Capsules, Soft", *Encyclopedia of Pharmaceutical Technology*, vol. 2, J. Swarbrick and J. C. Boylan, eds. (Marcel Dekker, Inc., New York, 1990) pp. 269–284; M. S. Patel et at., "Advances in Softgel Formulation Technology", *Manufacturing Chemist*, vol. 60, no. 7, pp. 26–28 (July 1989); M. S. Patel et al., "Softgel Technology", *Manufacturing Chemist*, vol. 60, no. 8, pp. 47–49 (August 1989); R. F. Jimerson, "Softgel (Soft Gelatin Capsule) Update", *Drug Development and Industrial Pharmacy* (Interphex '86 Conference), vol. 12, no. 8 & 9, pp. 1133–1144 (1986); and W. R. Ebert, "Soft Elastic Gelatin Capsules: A Unique Dosage Form", *Pharmaceutical Technology*, vol. 1, no. 5, pp. 44–50 (1977); these references are incorporated by reference herein in their entirety. The resulting soft gelatin capsule is soluble in water and in gatrointestinal fluids. Upon swallowing the capsule, the gelatin shell rapidly dissolves or ruptures in the gastrointestinal tract thereby introducing the xanthine derivatives from the shell and the pharmaceutical actives from the liquid core into the physiological system.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention.

Ingredients are identified by chemical or CTFA name.

EXAMPLE I

A soft gelatin capsule containing a concentrated liquid core composition is prepared from the following ingredients.

Liquid Core Composition

| Ingredient | Weight % |
| --- | --- |
| Ibuprofen | 23.00 |
| Polyethylene Glycol 600 | 50.00 |
| Polyvinylpyrrolidone[1] | 2.00 |
| Propylene Glycol | 13.00 |
| Water | QS100 |

[1] Available as Plasdone ® K-29/32 from GAF Chemicals Co.

The ibuprofen, polyethylene glycol 600, polyvinylpyrrolidone, propylene glycol and water are combined in a suitable vessel and warmed to 70° C. until a homogeneous solution is obtained.

Gelatin Capsule

| Ingredient | Weight % |
| --- | --- |
| Gelatin | 47.00 |
| Glycerin | 15.00 |
| Caffeine | 5.00 |
| Water | QS100 |

The above ingredients are combined in a suitable vessel and heated with mixing at about 65° C. to form a uniform solution. Using standard encapsulation methodology, the resulting solution is used to prepare soft gelatin capsules containing the liquid core composition formed above. The resulting soft gelatin ibuprofen capsules are suitable for oral administration.

EXAMPLE II

A soft gelatin capsule containing a concentrated liquid core composition is prepared from the following ingredients as described in Example I.

Liquid Core Composition

| Ingredient | Weight % |
| --- | --- |
| Naproxen | 28.00 |
| Polyethylene Glycol 600 | 48.00 |
| Polyvinylpyrrolidone[1] | 2.50 |
| Propylene Glycol | 5.00 |
| Water | QS100 |

[1] Available as Plasdone ® K-29/32 from GAF Chemicals Co.

Gelatin Capsule

A soft gelatin mixture is prepared from the following ingredients.

| Ingredient | Weight % |
| --- | --- |
| Gelatin | 47.00 |
| Glycerin | 15.00 |
| Pentoxifylline | 5.00 |
| Water | QS100 |

EXAMPLE III

A soft gelatin capsule containing a concentrated liquid core composition is prepared from the following ingredients as described in Example I.

Liquid Core Composition

| Ingredient | Weight % |
| --- | --- |
| Ketorolac Tromethamine | 30.00 |
| Polyethylene Glycol 600 | 40.00 |
| Polyvinylpyrrolidone[1] | 3.00 |
| Ethanol 95% USP | QS100 |

[1]Available as Plasdone ® K-29/32 from GAF Chemicals Co.

Gelatin Capsule

A soft gelatin capsule containing a concentrated liquid core composition is prepared from the following ingredients.

| Ingredient | Weight % |
| --- | --- |
| Gelatin | 47.00 |
| Glycerin | 15.00 |
| Pentoxifylline | 5.00 |
| Water | QS100 |

EXAMPLE IV

A soft gelatin capsule containing a concentrated liquid core composition is prepared from the following ingredients.

Liquid Core Composition

| Ingredient | Weight % |
| --- | --- |
| Acetaminophen | 26.00 |
| Polyethylene Glycol 600 | 52.00 |
| Polyvinylpyrrolidone[1] | 3.00 |
| Ethanol 95% USP | QS100 |

[1]Available as Plasdone ® K-29/32 from GAF Chemicals Co.

The acetaminophen, polyethylene glycol 600, polyvinylpyrrolidone, and ethanol are combined in a suitable vessel and mixed at room temperature until a homogeneous solution is obtained. Next, the ethanol is removed by rotary evaporation at room temperature. The resulting liquid core composition is encapsulated in the gelatin capsule described in Example I.

EXAMPLE V

A soft gelatin capsule containing a concentrated liquid core composition is prepared from the following ingredients.

Liquid Core Composition

| Ingredient | Weight % |
| --- | --- |
| Acetaminophen | 22.22 |
| Pseudoephedrine Hydrochloride | 2.67 |
| Dextromethorphan Hydrobromide | 0.89 |
| Guaifenesin | 8.89 |
| Polyethylene Glycol 600 | 40.00 |
| Polyvinylpyrrolidone[1] | 1.78 |
| Propylene Glycol | 13.56 |
| Ethanol 95% USP | QS100 |

[1]Available as Plasdone ® K-29/32 from GAF Chemicals Co.

The acetaminophen, pseudoephedrine hydrochloride, dextromethorphan hydrobromide, guaifenesin, polyethylene glycol 600, polyvinylpyrrolidone, propylene glycol, and ethanol are combined in a suitable vessel and mixed at room temperature until a homogeneous solution is formed. Next, the ethanol is removed by rotary evaporation. The resulting liquid core composition is encapsulated in the gelatin capsule described in Example I.

What is claimed is:

1. A pharmaceutical composition in the form of a soft gelatin capsule of a size suitable for easy swallowing and typically containing from about 100 mg to about 2000 mg of a solubilized pharmaceutical active composition, comprising:

a) an outer gelatin shell containing a xanthine derivative incorporated into the soft gelatin of the outer shell; and b) a concentrated liquid core composition, which is encapsulated by said outer gelatin shell, comprising a solvent solution of a safe and effective mount of at least one solubilized analgesic pharmaceutical active; said soft gelatin capsule upon swallowing dissolves or ruptures in the gastrointestinal tract thereby introducing the xanthine derivatives from the outer galatin shell and the pharmaceutical actives from the liquid core composition into the physiological system.

2. A pharmaceutical composition according to claim 1 wherein said concentrated liquid core composition comprises a solvent selected from the group consisting of polyethylene glycol, polyvinylpyrrolidone, propylene glycol and monohydric alcohols having from one to four carbon atoms and mixtures thereof.

3. A pharmaceutical composition according to claim 2 wherein said solvent comprises from about 20% to about 70% of a polyethylene glycol and from about 1% to about 28% of a polyvinylpyrrolidone.

4. A process according to claim 3 wherein said analgesic active is selected from the group consisting of acetaminophen, acetylsalicylic acid, ibuprofen, fenbuprofen, fenoprofen, flurbiprofen, indomethacin, naproxen, pharmaceutically-acceptable salts thereof and mixtures thereof.

5. A process according to claim 4 wherein said polyethylene glycol is selected from the groups consisting of PEG-6, PEG-8, PEG-9, PEG-10, PEG-12, PEG-14, PEG-16, PEG-18, PEG-20, and mixtures thereof.

6. A process according to claim 5 wherein said polyethylene glycol is PEG- 12.

7. A process according to claim 6 wherein said polyvinylpyrrolidone has an average molecular weight of about 9,000 to about 45,000.

8. A process according to claim 7 wherein said polyvinylpyrrolidone has an average molecular weight of about 29,000.

9. A pharmaceutical composition according to claim 2 which further comprises an additional pharmaceutical active selected from the group consisting of analgesics, decongestants, expectorants, antitussives, and antihistamines and mixtures thereof.

10. A pharmaceutical composition according to claim 9 wherein said additional pharmaceutical active is selected from the group consisting of dextromethorphan hydrobromide, doxylamine succinate, pseudoephedrine hydrochloride, chlorpheniramine maleate, guaifenesin, triprolidine hydrochloride, diphenhydramine hydrochloride, and mixtures thereof.

* * * * *